(12) United States Patent
Kurr et al.

(10) Patent No.: US 11,014,864 B2
(45) Date of Patent: *May 25, 2021

(54) METHOD FOR PRODUCING CATALYSTS HAVING INCREASED STRENGTH AND DECREASED VOLUME REDUCTION

(71) Applicant: Clariant International Ltd., Muttenz (CH)

(72) Inventors: Patrick Kurr, Moenchgladbach (DE);
Benjamin Kniep, Heufeld (DE);
Andrea Blindhuber, Kolbermoor (DE);
Verena Pritscher, Grosskarolinenfeld (DE)

(73) Assignee: Clariant International Ltd., Muttenz (CH)

(*) Notice: Subject to any disclaimer, the term of this patent is extended or adjusted under 35 U.S.C. 154(b) by 0 days.

This patent is subject to a terminal disclaimer.

(21) Appl. No.: 15/128,878

(22) PCT Filed: Mar. 19, 2015

(86) PCT No.: PCT/EP2015/055759
§ 371 (c)(1),
(2) Date: Sep. 23, 2016

(87) PCT Pub. No.: WO2015/144549
PCT Pub. Date: Oct. 1, 2015

(65) Prior Publication Data
US 2017/0121259 A1 May 4, 2017

(30) Foreign Application Priority Data
Mar. 26, 2014 (DE) .................. 10 2014 004 391.6

(51) Int. Cl.
| | | |
|---|---|---|
| *B01J 23/80* | (2006.01) | |
| *B01J 35/02* | (2006.01) | |
| *B01J 35/10* | (2006.01) | |
| *B01J 37/02* | (2006.01) | |
| *B01J 37/03* | (2006.01) | |
| *B01J 37/04* | (2006.01) | |
| *B01J 37/06* | (2006.01) | |
| *B01J 37/08* | (2006.01) | |
| *B01J 37/18* | (2006.01) | |
| *C07C 29/154* | (2006.01) | |
| *B01J 35/00* | (2006.01) | |
| *B01J 37/00* | (2006.01) | |
| *C01B 32/50* | (2017.01) | |
| *B01J 21/02* | (2006.01) | |

(52) U.S. Cl.
CPC .......... *C07C 29/154* (2013.01); *B01J 21/02* (2013.01); *B01J 23/80* (2013.01); *B01J 35/002* (2013.01); *B01J 35/0006* (2013.01); *B01J 35/023* (2013.01); *B01J 35/026* (2013.01); *B01J 35/1014* (2013.01); *B01J 35/1019* (2013.01); *B01J 35/1038* (2013.01); *B01J 37/0009* (2013.01); *B01J 37/0063* (2013.01); *B01J 37/0236* (2013.01); *B01J 37/031* (2013.01); *B01J 37/04* (2013.01); *B01J 37/06* (2013.01); *B01J 37/08* (2013.01); *B01J 37/18* (2013.01); *C01B 32/50* (2017.08); *B01J 2523/00* (2013.01); *Y02P 20/52* (2015.11)

(58) Field of Classification Search
CPC ... B01J 23/72; B01J 23/80; B01J 21/02; B01J 35/1014; B01J 37/0236; B01J 37/031; B01J 37/04; B01J 37/08; B01J 37/18
See application file for complete search history.

(56) References Cited

U.S. PATENT DOCUMENTS

| | | | | |
|---|---|---|---|---|
| 3,850,850 A * | 11/1974 | Collins | ................ | B01J 23/80 502/307 |
| 4,257,920 A * | 3/1981 | Sugier | ................ | C01B 3/16 502/302 |
| 4,535,071 A | 8/1985 | Schneider | | |
| 4,596,782 A * | 6/1986 | Courty | ................ | B01J 23/80 252/373 |
| 5,019,547 A * | 5/1991 | Chaumette | ................ | B01J 37/03 502/342 |
| 6,455,464 B1 | 9/2002 | Chen | | |
| 6,500,403 B2 | 12/2002 | Ward | | |
| 6,576,217 B1 * | 6/2003 | Nojima | ................ | B01J 23/80 252/373 |
| 6,919,066 B2 | 7/2005 | Holzle | | |
| 7,510,591 B2 * | 3/2009 | Huber-Dirr | ................ | B01J 23/83 75/233 |
| 7,754,651 B2 | 7/2010 | Ladebeck | | |
| 7,820,128 B2 | 10/2010 | Polier | | |
| 8,623,927 B2 | 1/2014 | Kang | | |
| 10,035,137 B2 | 7/2018 | Paulus | | |

(Continued)

FOREIGN PATENT DOCUMENTS

| | | |
|---|---|---|
| DE | 10160487 | 6/2003 |
| EP | 2357037 | 8/2011 |

(Continued)

*Primary Examiner* — Jun Li

(57) ABSTRACT

The invention relates to a process for producing copper-containing catalysts, in particular shaped catalyst bodies having increased mechanical strength and a low volume shrinkage, and also the shaped catalyst bodies produced by the process of the invention and the use thereof as catalysts or as precursors and components for catalysts. The catalysts of the invention are particularly suitable for the synthesis of methanol and for the low-temperature conversion of CO into $CO_2$.

15 Claims, No Drawings

(56) References Cited

U.S. PATENT DOCUMENTS

| | | | | |
|---|---|---|---|---|
| 2001/0024632 A1* | 9/2001 | Ward | ................ | B01J 23/80 |
| | | | | 423/437.2 |
| 2002/0169075 A1* | 11/2002 | Holzle | ............. | B01J 23/80 |
| | | | | 502/342 |
| 2009/0048355 A1* | 2/2009 | Polier | ............. | B01J 23/80 |
| | | | | 518/711 |
| 2011/0118367 A1* | 5/2011 | Kang | .............. | B01J 23/002 |
| | | | | 518/713 |
| 2015/0314273 A1* | 11/2015 | Paulus | ............ | B01J 37/031 |
| | | | | 502/324 |

FOREIGN PATENT DOCUMENTS

| | | | | |
|---|---|---|---|---|
| JP | S59-189937 | | 10/1984 | |
| WO | WO-2014048957 A1 * | | 4/2014 | ........... B01J 37/031 |

\* cited by examiner

METHOD FOR PRODUCING CATALYSTS HAVING INCREASED STRENGTH AND DECREASED VOLUME REDUCTION

The invention relates to a process for producing copper-containing catalysts, in particular shaped catalyst bodies having increased mechanical strength and a low volume shrinkage, and also the shaped catalyst bodies produced by the process of the invention and the use thereof as catalysts or as precursors and components for catalysts. The catalysts of the invention are particularly suitable for the synthesis of methanol and for the low-temperature conversion of CO into $CO_2$.

BACKGROUND OF THE INVENTION

Copper-containing catalysts are used on a large scale in the production of basic and fine chemicals, e.g. in the catalytic conversion of mixtures of $CO_2$, CO and $H_2$ into methanol. The properties of such catalysts can be varied as a function of various parameters, e.g. by the choice of support material or via the size and shape of the metal particles. The activity of these catalysts having copper as active component is generally dependent on the size of the metal particles.

Copper-containing catalysts are often produced by means of a multistage process. Here, a catalyst precursor material is produced in a first step from the copper component and also further components which have a stabilizing support function on the active component in the future catalyst. This is usually effected by coprecipitation of all desired components. After washing to remove excess salts or undesirable (alkali) metals, drying is carried out to give a solid catalyst precursor material. In a further step, this solid catalyst precursor is treated thermally and converted into a largely oxidic state. This is followed by shaping of the catalyst composition by tableting, granulation, extrusion or by a combination of the methods mentioned. Finally, the shaped body obtained is converted by means of hydrogen, carbon monoxide or wet-chemical reducing agents into the catalytically active, finely divided copper metal.

Methanol synthesis plants are usually charged with the oxidic catalyst in pellet form and this is subsequently converted in-situ into the catalytically active catalyst by means of reduction in a stream of hydrogen according to appropriate activation processes.

For example, DE 10 2005 020 630-A1, WO 03/053569, DE 3317 725 A1 and DE 101 60 487 A1 describe the production of copper-based catalysts for the synthesis of methanol.

However, the catalysts produced in the manner described have the disadvantage that they suffer from pronounced volume shrinkage as a result of reduction, which is also associated with a significant decrease in the mechanical strength of the shaped body. There are many reasons for the pronounced volume shrinkage of copper-containing shaped catalyst bodies during reduction. For example, the shaped body can shrink due to the volume contraction during transformation from the oxidic state into the metallic state. Further reasons are the condensation of water vapor which is usually formed in the reduction, which can lead to collapse of the pore structure of the shaped catalyst body. However, a very low volume shrinkage of the shaped body is desirable for optimal utilization of the catalyst bed in the reactor during operation. An increased volume shrinkage of the catalyst bed in the reactor leads to poorer utilization of the reactor (part of the reactor remains empty) and poorer utilization of the heat transfer area of the reactor. The latter is particularly problematical since cooling of the catalyst bed usually represents a limiting factor during operation.

In principle, the reduction step can also be carried out before loading of the reactor with the catalyst by reduction and subsequent passivation under mild conditions by means of an oxidant, generally by means of gaseous oxygen (reduction stabilization) or by wet-chemical stabilization by means of an oil. However, the copper catalysts produced in this way usually have the disadvantages that (i) a further process step associated with additional costs is necessary in production of the catalyst, that (ii) the copper catalyst has a significantly lower mechanical strength compared to the unreduced (oxidic) state, which shows up, in particular, by increased fracture in the catalyst bed compared to the oxidic state during loading of the reactor, and that (iii) the reduction-stabilized catalysts are not storage-stable and reoxidize by contact with air over time. Here, reference may be made, for example, to the document EP 1 238 702 A1.

A high mechanical strength is demanded of shaped bodies, e.g. pellets, so that they can survive the stresses which act on them at the time of charging of the reactor and also during operation without suffering damage. However, the reduction of catalysts is generally also associated with a significant reduction in the mechanical strength. Particularly in the case of reduced metal catalysts in the form of pellets, the lateral compressive strength, as a measure of the mechanical strength of pellets, is many times lower compared to the lateral compressive strength in the oxidic state. Correspondingly, the mechanical strength of the pellets is also many times lower after reduction than in the oxidic state. As a result of vibrations, external and internal pressure fluctuations in the reactor during operation and/or the weight of the catalyst bed on the individual shaped catalyst bodies, the pellets are highly stressed during operation by rubbing against the reactor wall or by rubbing of the pellets against one another, which in particular as a result of the stresses arising at the edges and corners of the pellets leads to increased abrasion of the pellets.

It is therefore an object of the present invention to provide a production process by means of which copper-containing shaped catalyst bodies having greatly reduced, preferably absolutely no, volume shrinkage after activation (reduction to the metal) combined with high mechanical strength can be obtained. The process should also be simple to carry out and inexpensive. The catalysts obtained should preferably be able to be used for the synthesis of methanol.

SUMMARY OF THE INVENTION

The invention provides a process for producing a shaped catalyst body containing copper, zinc and aluminum, which comprises the following steps:

(a) combining of an alkaline solution, in particular a carbonate-containing precipitant,
   with a copper-containing solution, which is obtainable by dissolving and/or suspending a copper compound, a zinc compound and an aluminum compound,
   to give a precipitate;
(b) isolation, optionally washing and/or optionally drying of the precipitate to give a solid catalyst precursor;
(c) thermal treatment at a temperature in the range from 200° C. to 600° C. of the solid catalyst precursor obtained in step (b) to give a mixed oxide, preferably a mixed oxide having a BET surface area in the range from 80 $m^2$/g to 140 m²/g, more preferably in the range from 85 m²/g to 120 m²/g, particularly preferably in the range from 90 m²/g to 110 m²/g;

(d) mixing of solid catalyst precursor obtained in step (b) with mixed oxide obtained in step (c) in a weight ratio of solid catalyst precursor to mixed oxide in the range from 2:98 to 20:80, preferably in the range from 5:95 to 15:85, more preferably in the range from 10:90 to 15:85, to give a mixture; and (e) tableting of the mixture obtained in step (d).

In addition, the invention provides shaped catalyst bodies which can be produced by the process of the invention.

The invention also provides for the use of shaped catalyst bodies produced by the process of the invention for the synthesis of methanol from synthesis gas containing $CO_2$, CO and $H_2$ or for the low-temperature conversion of CO into $CO_2$.

DETAILED DESCRIPTION OF THE INVENTION

The process of the invention for producing a shaped catalyst body comprises combining of a copper-containing solution with an alkaline solution to form a precipitate in step (a).

The copper-containing solution is produced by dissolving and/or suspending a copper compound, a zinc compound and an aluminum compound in a suitable solvent in a vessel. As an alternative, a copper compound, a zinc compound and an aluminum compound can be dissolved and/or suspended in a plurality of vessels and the resulting solutions can be combined to give the copper-containing solution.

For the purposes of the present invention, the formulation "solution" includes both solutions and also suspensions and slurries, with solutions and suspensions being preferred.

The solvent for producing the copper-containing solution (or for producing the individual solutions which are combined to produce the copper-containing solution) is preferably water or an aqueous acid such as aqueous hydrochloric acid (HCl), aqueous nitric acid ($HNO_3$), aqueous sulfuric acid or mixtures thereof, in particular water or aqueous nitric acid.

The copper-containing aqueous solution preferably has a pH in the range from 0 to 7, more preferably in the range from 1 to 5, particularly preferably in the range from 2 to 4.

As copper compounds, it is in principle possible to use both copper in metallic form and preferably all compounds of copper which are readily soluble in water, acids or alkalis, in particular the compounds of copper which are readily soluble in water and/or acids, in particular the salts of copper, very particularly the nitrates; sulfates; halides such as chlorides, bromides and/or iodides; carbonates; oxides; hydroxides; hydrogencarbonates and/or acetates of copper. The copper compound is preferably copper nitrate. Particular preference is given to using an aqueous, in particular acid, copper nitrate solution in the process of the invention.

As zinc compounds, it is in principle possible to use both copper in metallic form and preferably all compounds of zinc which are readily soluble in water, acids or alkalis, in particular the compounds of zinc which are readily soluble in water and/or acids, in particular the salts of zinc, very particularly the nitrates; sulfates; halides such as chlorides, bromides and/or iodides; carbonates; oxides; hydroxides; hydrogencarbonates and/or acetates of zinc. The zinc compound is preferably zinc nitrate. Particular preference is given to using an aqueous, in particular acidic, zinc nitrate solution in the process of the invention.

As aluminum compounds, it is in principle possible to use both aluminum in metallic form and preferably all compounds of aluminum which are readily soluble in water, acids or alkalis, in particular the salts of aluminum, very particularly preferably the nitrates; sulfates; halides such as chlorides, bromides and/or iodides; oxides; hydroxides and/or acetates of aluminum. The aluminum compound is preferably aluminum nitrate.

Further preferred aluminum compounds include sodium aluminates and aluminum hydroxide sols and mixtures thereof.

As aluminum hydroxide sol, it is possible to use, for example, a commercially available product, e.g. a peptized boehmite or pseudo boehmite. In this case, a suspension comprising copper, zinc and aluminum compounds is formed by combining of the copper and zinc compounds with the aluminum hydroxide sol. As an alternative, the aluminum hydroxide sol can also be obtained by combining an aqueous, alkaline sodium aluminate solution (pH>9) with an acidic copper and zinc salt solution (pH<1). In this case, a preprecipitated, acidic suspension (pH≤3.0) containing copper, zinc and aluminum compounds is formed by combining of the copper, zinc and aluminum compounds.

The alkaline solution is, in particular, produced by dissolving alkali metal compounds, alkaline earth metal compounds and/or ammonium compounds, in particular alkali metal and/or ammonium compounds, particularly preferably carbonates, hydrogencarbonates and/or hydroxides thereof, in a suitable solvent, in particular water.

The alkali metal compounds, alkaline earth metal compounds and ammonium compounds are preferably selected from the group consisting of alkali metal carbonates such as lithium, sodium, potassium, rubidium or cesium carbonate, alkali metal hydroxides such as lithium, sodium or potassium hydroxide, alkaline earth metal carbonates such as magnesium, calcium, strontium or barium carbonate, ammonium carbonate, ammonium hydroxide and mixtures thereof. It is likewise possible to use the corresponding hydrogencarbonates or any mixtures of carbonates and hydrogencarbonates simultaneously with or instead of the carbonates.

An aqueous alkali metal and/or ammonium carbonate solution, an aqueous alkali metal and/or ammonium hydrogencarbonate solution, an aqueous alkali metal and/or ammonium hydroxide solution, in particular an aqueous sodium carbonate solution, an aqueous sodium hydrogencarbonate solution and/or an aqueous ammonium hydroxide solution ($NH_3$ in water), particularly preferably an aqueous sodium carbonate solution and/or an aqueous sodium hydrogencarbonate solution, is preferably used as alkaline solution.

The alkaline aqueous solution preferably has a basic pH in the range from 7 to 14, more preferably in the range from 8 to 14, particularly preferably in the range from 10 to 13.

Combining of the copper-containing solution (which contains copper, zinc and aluminum) with the alkaline solution results in formation of a precipitate.

In one embodiment, the combining can be carried out by introducing the abovementioned solutions simultaneously into a joint vessel, for example a precipitation vessel. In this case, the two solutions are introduced, preferably continuously, into the reaction volume of a precipitation mixer. In a further embodiment, combining can also be effected by introducing the one solution into the other solution which has been initially charged, for example in a vessel such as a precipitation vessel. In a preferred embodiment, combining of the solutions is effected by introducing a volume stream of the copper-containing solution into the appropriate alkaline solution which has been initially placed in a precipitation vessel.

Before the combining, the copper-containing solution is preferably heated to a temperature of 20° C. or more, for example to a temperature in the range from 50° C. to 90° C., in particular to about 65° C., and preferably stirred.

The alkaline solution is likewise preferably heated to a temperature of 20° C. or more, for example to a temperature in the range from 50° C. to 90° C., in particular to about 65° C., and stirred before the combining.

In a preferred embodiment, both the copper-containing solution and the alkaline solution are heated to a temperature in the range from 50° C. to 90° C., in particular to about 65° C., and stirred.

When solutions of the abovementioned solution pairs are combined, a precipitate is formed in the mixture (hereinafter also referred to as precipitate-containing solution mixture). Combining of the solutions is generally carried out in a stirred vessel. The vessel is preferably stirred by means of an inclined blade stirrer, propeller stirrer or other commercial stirrers.

The precipitate-containing solution mixture is preferably maintained at a temperature of 20° C. or more and in particular at a temperature in the range from 50° C. to 90° C., preferably at about 65° C. In a particularly preferred embodiment of the invention, the precipitate-containing solution mixture is maintained at a temperature in the range from 50° C. to 90° C., preferably at a temperature of about 65° C., for at least 30 minutes, preferably from 1 hour to 36 hours, in particular about hours, in order to complete the formation of the precipitate if necessary or to increase the crystallinity of the precipitate by aging.

Until precipitate formation is complete, the pH of the precipitate-containing solution mixture is usually kept constant by methods known to those skilled in the art. For example, the rate of introduction of solutions can be selected so that a particular pH is established in the precipitate-containing solution mixture. The pH of the precipitate-containing solution mixture is preferably in the range from 5.0 to 8.5, in particular in the range from 6.0 to 7.5, preferably about 6.5.

The precipitate obtained in step (a) is preferably separated off by filtration in step (b). As an alternative, the precipitate can be separated off by decantation or centrifugation.

The isolated precipitate is optionally subjected to one or more washing steps and subsequently optionally dried. Isolation, optionally washing and optionally drying of the precipitate gives a solid catalyst precursor.

The washing of the precipitate can, for example, be carried out by firstly separating the precipitate-containing solution mixture from the precipitate by use of a filter press and subsequently passing water through the material in the filter press, thereby washing the material. As an alternative, the isolated precipitate can, after the precipitate-containing solution mixture has been separated off by filtration, decantation or centrifugation, be slurried in a vessel and subsequently separated off from the liquid phase again by means of a filter press, a centrifuge or a decanter. This procedure is generally carried out one or more times until a particular content of sodium ions in the filter residue, i.e. in the filtercake, has been reached. The content of sodium ions can be determined by atomic absorption spectroscopy (AAS). The content of sodium in the filtercake after the last washing operation is preferably 500 ppm or less, more preferably less than 400 ppm or less, in particular 350 ppm or less. As an alternative, washing can also be carried out until a particular conductivity of the filtrate has been reached. Here, the conductivity generally correlates with the concentration of sodium ions. The conductivity of the filtrate from the last washing operation is preferably 0.5 mS/cm or less, in particular 0.2 mS/cm or less. The conductivity is determined in accordance with DIN 38404, part 8.

The isolated and optionally washed precipitate is then preferably subjected to drying. Drying is carried out by heating the precipitate to a temperature in the range from 75° C. to 130° C., preferably in the range from 105° C. to 115° C.

In a particularly preferred embodiment, drying is carried out by spray drying. For this purpose, a suspension having a solids content of 10 to 40% by weight is produced from the isolated precipitate, e.g. a filtercake, by means of water. This suspension is then preferably introduced via a nozzle into a spray dryer. The temperature in the spray dryer during drying is preferably in the range from 75° C. to 130° C., in particular in the range from 105° C. to 115° C. The output temperature characteristic for drying is preferably in the range from 105° C. to 115° C. and is usually controlled via parameters such as amount of suspension sprayed in, the solids content of the suspension (and thus the amount of water which has to be evaporated) or temperature in the spray dryer. The treatment of the material by means of the spray dryer results, in particular, in a dry powder.

Part of the solid catalyst precursor obtained in step (b) is subjected to a thermal treatment in step (c), giving a mixed oxide.

In the thermal treatment, the metals are (at least partially) converted into the corresponding oxides by decomposition of the carbonates in the optionally spray-dried precursor material. The specific BET surface area is in the range from 80 $m^2/g$ to 140 $m^2/g$, preferably in the range from 85 $m^2/g$ to 120 $m^2/g$, particularly preferably in the range from 90 $m^2/g$ to 110 $m^2/g$. This can be controlled via the temperature and duration of the thermal treatment (calcination). Preferred calcination temperatures are in the range from 200° C. to 600° C., preferably in the range from 270° C. to 550° C. and particularly preferably in the range from 450° C. to 500° C. The duration of the thermal treatment is preferably from 1 hour to 5 hours, more preferably from 2.5 hours to 4 hours, particularly preferably about 3 hours.

In a particularly preferred embodiment, the thermal treatment is carried out for a period of from 2.5 hours to 4 hours at a temperature in the range from 450° C. to 500° C.

The thermal treatment can be carried out in air, in oxygen or under protective gas such as argon or nitrogen or mixtures thereof. The thermal treatment can be carried out batchwise, e.g. in a tray furnace, or continuously, e.g. in a rotary tube furnace.

In step (d), the mixed oxide obtained in step (c) is mixed with part of the solid catalyst precursor obtained in step (b) (which has not been subjected to a thermal treatment). The weight ratio of solid (not thermally treated) catalyst precursor to thermally treated catalyst precursor (mixed oxide) is in the range from 2:98 to 20:80, preferably in the range from 5:95 to 15:85, more preferably in the range from 10:90 to 15:85.

The mixture obtained in step (d) is subsequently (preferably with addition of lubricant) tableted in a step (e).

Tableting is preferably carried out by means of a tableting press, for example a Korsch tableting press. Pellets having a diameter d of from 1 mm to 10 mm, preferably from 1.5 mm to 8 mm and particularly preferably from 4 mm to 6 mm, and a height h of from 1 mm to 10 mm, preferably from 1.5 mm to 8 mm and particularly preferably from 3 mm to 4 mm, can be obtained by means of the tableting operation.

Tableting is preferably carried out with addition of a lubricant such as graphite, oils or stearates, in particular graphite. The mixture obtained (in step (d)) of thermally treated mixed oxide (from step (c)) and solid catalyst precursor (from step (b)) is mixed with lubricants, in particular graphite, optionally compacted and/or granulated and then tableted in step (e). The lubricant is preferably added before tableting in an amount in the range from 0.1 to 5% by weight, based on the total weight of the composition to be tableted. The lubricant is more preferably added in an amount in the range from 0.5 to 5% by weight, particularly preferably in an amount in the range from 1 to 3° by weight, preferably about 2% by weight, based on the total weight of the composition to be tableted.

The shaped catalyst body obtained after tableting preferably has a lateral compressive strength based on the pellet weight, measured in accordance with DIN EN 1094-5, in the range of 550 N/g or more, preferably in the range from 600 N/g to 1300 N/g, in particular in the range from 600 to 900 N/g.

In a preferred embodiment, the tableted shaped catalyst bodies have a diameter d in the range from 4 mm to 6 mm and a height h in the range from 3 mm to 4 mm, and have a lateral compressive strength, based on the pellet weight, in the range from 600 to 900 N/g.

The tableted shaped catalyst bodies preferably have a loss on ignition of 7.5% by weight or less, preferably 5.5% by weight or less, in particular in the range from 0.1 to 4.0% by weight.

In a further preferred embodiment, the shaped catalyst body obtained has a lateral compressive strength based on the pellet weight, measured in accordance with DIN EN 1094-5, in the range from 600 to 900 N/g and a loss on ignition in the range from 0.1 to 4.0% by weight.

In a further embodiment, the tableted mixture obtained in step (e) is reduced in a further step (f).

Reduction is preferably effected by heating the tableted shaped catalyst body in a reducing atmosphere. In particular, the reducing atmosphere is hydrogen. Reduction is, for example, carried out at a temperature in the range from 150° C. to 450° C., in particular in the range from 180° C. to 300° C., preferably in the range from 190° C. to 290° C., particularly preferably at about 250° C.

Reduction is, for example, carried out, depending on the amount of catalyst to be reduced, for a period of from 1 hour (for, for example, 500 g) to 10 days (for, for example, 60 metric tons), in particular for a period of from 2 hours to 120 hours, preferably for a period of from 24 to 48 hours. Amounts of catalyst corresponding to the production scale (for example in the range from 1 to 60 metric tons) are preferably reduced for a period of from 3 to 8 days. In a preferred embodiment, reduction is carried out at a temperature in the range from 190° C. to 210° C.

After reduction, the shaped catalyst bodies are preferably stabilized wet or dry. In the case of wet stabilization, the shaped bodies are covered with liquid in order to avoid contact with oxygen as far as possible. Suitable liquids include organic liquids and water, preferably organic liquids. Preferred organic liquids are those which at 20° C. have a vapor pressure of 0.5 hPa or less. Examples of suitable organic liquids are isodecanol, fatty alcohols such as Nafol® from Sasol, hexadecane, 2-ethylhexanol, propylene glycol and mixtures thereof, in particular isodecanol.

In the case of dry stabilization, a mixture of oxygen or an oxygen-containing gas, preferably air, and an inert gas such as argon or nitrogen is introduced into the reduction reactor. The concentration of oxygen in the mixture is preferably increased from about 0.04° by volume to about 21% by volume. For example, a mixture of air and inert gas can be introduced, with the ratio of air to inert gas initially being about 0.2% by volume of air to 99.8% by volume of inert gas. The ratio of air to inert gas is then gradually increased (e.g. continuously or stepwise) until finally 100% by volume, for example, of air is introduced (which corresponds to an oxygen concentration of about 21% by volume). Without wishing to be tied to a theory, it is presumed that the introduction of air or oxygen results in formation of a thin oxide layer having a thickness of, for example, from 0.5 nm to 50 nm, preferably from 1 nm to 20 nm, in particular from 1 nm to 10 nm, on the surface of the catalyst, which protects the catalyst against further oxidation. In dry stabilization, the reactor temperature is preferably 100° C. or less, more preferably from 20° C. to 70° C. and particularly preferably from 30° C. to 50° C. After the stabilization, the catalyst is transportable and can be transported to the user/plant operator.

The volume shrinkage of the pellets after reduction and passivation is determined by measuring the pellet dimensions (diameter and height) of a representative number of 20 pellets.

The shaped catalyst bodies produced by the process of the invention display, in a particular embodiment, a volume shrinkage due to reduction of 8% or less, preferably 6% or less, in particular 5% or less.

The Cu/Zn atomic ratio in the shaped catalyst body can vary within wide limits, but is preferably matched to that of conventional methanol synthesis catalysts. The Cu/Zn atomic ratio in the shaped catalyst body is preferably from 15:85 to 85:15, particularly preferably from 60:40 to 75:25. The Zn/Al atomic ratio is preferably from 60:40 to 80:20, particularly preferably from 70:30 to 80:20.

In one preferred embodiment the Cu/Zn atomic ratio is from 15:85 to 85:15 and the Zn/Al atomic ratio is from 60:40 to 80:20. In one particularly preferred embodiment the Cu/Zn atomic ratio is from 60:40 to 75:25 and the Zn/Al atomic ratio is from 70:30 to 80:20.

The copper-containing shaped catalyst body of the invention is suitable for industrial use. The term "shaped catalyst body" can, for the purposes of the present invention, be used interchangeably with the term "catalyst", in particular when the function as such is under discussion.

The invention also provides for the use of the above-described catalyst for the synthesis of methanol from synthesis gas, i.e. from gas containing $CO_2$, CO and $H_2$. The synthesis gas usually consists of from 5% by volume to 25% by volume of carbon monoxide, from 6% by volume to 12% by volume of carbon dioxide, from 10% by volume to 30% by volume of inert gases, e.g. nitrogen and/or methane, with hydrogen as balance.

The methanol synthesis is usually carried out at a temperature in the range from 200° C. to 300° C., preferably in the range from 210° C. to 280° C., at a pressure in the range from 40 bar to 150 bar, preferably in the range from 60 bar to 100 bar, and a space velocity in the range from 2000 to 22 000 $h^{-1}$. The space velocity is defined as the ratio of the volume flow of synthesis gas to the spatial volume of the catalyst, e.g. of a catalyst bed, based on the time unit of 1 hour.

The copper-containing catalyst of the invention is also suitable for the conversion of CO into $CO_2$, in particular the low-temperature conversion of CO into $CO_2$. The conversion of CO into $CO_2$ occurs according to the following reaction equation:

$$CO+H_2O\Longleftrightarrow H_2+CO_2$$

The low-temperature conversion is usually carried out at a temperature in the range from 170° C. to 270° C., preferably in the range from 190° C. to 240° C. The low-temperature conversion is usually carried out at a pressure in the range from 1 bar to 40 bar, preferably in the range from 10 bar to 35 bar. In a preferred embodiment, the low-temperature conversion is carried out at a temperature in the range from 170° C. to 270° C. and a pressure in the range from 1 bar to 40 bar, in particular at a temperature in the range from 190° C. to 240° C. and a pressure in the range from 10 bar to 35 bar.

Determination of Physical Parameters

The physical parameters indicated in the present invention are, unless indicated otherwise, determined as described below:

Determination of the BET surface area: The BET surface area is determined by the nitrogen single-probe method in accordance with DIN 66132 on the pulverulent catalyst and on pellets having a diameter of 6 mm and a height of 4 mm.

Determination of the loss on ignition: The determination of the loss on ignition is carried out starting from the powder. To determine the loss on ignition of the pellets, these are milled beforehand to give powder. The sample to be determined is weighed out into a porcelain crucible which has previously been ignited at 600° C. for 3 hours in a muffle furnace. The sample weighed into the ignited and tared porcelain crucible is subsequently thermally treated at 600° C. for 3 hours in a muffle furnace, transferred to a desiccator and cooled to room temperature. The cooled crucible is reweighed. The loss on ignition at 600° C. is determined from the mass difference.

Determination of the lateral compressive strength: The lateral compressive strength (LCS) of the shaped bodies/pellets is determined in accordance with DIN EN 1094-5, 1995-09 edition, refractory results for insulation purposes—part 5: "Bestimmung der Kaltdruckfestigkeit geformter Erzeugnisse". The determination is carried out using a commercial instrument, for example model SCHLEUNIGER 6-D or ERWEKA TBH 310 MD, in accordance with the instrument manufacturer's instructions. Typically, the pressures applied to the cylindrical wall of the pellets when rupture occurs is determined for a plurality of pellets (e.g. from 10 to 100, preferably from 10 to 30, for example 20 pellets). The arithmetic mean of the values obtained (in N) is formed. The lateral compressive strength based on the pellet weight (in N/g) is given by normalization of the arithmetic mean obtained for the lateral compressive strength on the basis of the arithmetic mean pellet weight.

Determination of the pore volume of the pellets: The pore volume is determined by the mercury intrusion method in accordance with DIN 66133 on pulverulent oxidic catalyst and on pellets.

EXAMPLES

The invention will be illustrated in more detail with the aid of the following, nonlimiting examples. Even though these examples describe specific embodiments of the invention, they serve merely to illustrate the invention and should not be interpreted as limiting the invention in any way. As a person skilled in the art will know, numerous modifications can be carried out on these without going outside the scope of protection of the invention as defined by the accompanying claims.

Production of the Catalysts

To produce the catalysts, a 14% strength by weight aqueous sodium carbonate solution was prepared and heated to 50° C. In a second vessel, 820 g of copper nitrate, 120 g of zinc oxide and 260 g of aluminum nitrate were dissolved in 900 g of water and 270 g of 68% strength by weight $HNO_3$ at 50° C. The nitrate solution and the sodium carbonate solution were brought together simultaneously at a temperature of 65° C. while keeping the pH of 6.5 constant (precipitation). The suspension was continuously pumped from the precipitation vessel into an aging vessel. After the precipitation was complete, the suspension was aged at 70° C. for at least 120 minutes. The color changed from light blue (commencement of aging) to green (end of aging). After aging, the suspension was filtered and the filtercake was washed until the sodium content of the filtercake, determined by atomic absorption spectroscopy, was less than 350 ppm. The filtercake was slurried by addition of water to an oxide concentration of 10% by weight and dried in a spray dryer at an inlet temperature of from 275° C. to 270° C. and an outlet temperature of from 105° C. to 115° C. to give a solid catalyst precursor. The solid catalyst precursor obtained was used for production of the shaped catalyst bodies described below.

For the analytical determination of the composition, part of the solid catalyst precursor was calcined at 330° C. for 2 hours. The chemical composition (in % by weight) was as follows: 64.0% of CuO, 27.8% of ZnO, 8.2% of $Al_2O_3$. The solid catalyst precursor was subsequently thermally treated at various temperatures (step (c)) and in the case of the shaped catalyst bodies according to the invention mixed in the indicated ratio with solid catalyst precursor material which had not been thermally treated (step (d)). Finally, the mixture was tableted with addition of in each case 2% by weight of graphite, based on the weight of the mixture, to give pellets having a diameter of 6 mm and a height of 4 mm (step (e)).

Comparative catalyst 1 (Ex11519.01): The thermal treatment was carried out at 400° C. in a muffle furnace for 3 hours. The powder obtained had a BET surface area of 119 $m^2/g$ and a loss on ignition of 11.9% by weight. 100 g of the powder were subsequently mixed with 2 g of graphite and the mixture was tableted to give shaped bodies having a diameter of 6 mm and a height of 4 mm. The lateral compressive strength based on the pellet weight was 1021.5 N/g.

Comparative catalyst 2 (Ex11519.02): The thermal treatment was carried out at 430° C. in a muffle furnace for 3 hours. The powder obtained had a BET surface area of 117 $m^2/g$ and a loss on ignition of 9.0% by weight. 100 g of the powder were subsequently mixed with 2 g of graphite and the mixture was tableted to give shaped bodies having a diameter of 6 mm and a height of 4 mm. The lateral compressive strength based on the pellet weight was 1020.4 N/g.

Catalyst 1 (Ex11519.04): The thermal treatment was carried out at 460° C. in a muffle furnace for 3 hours. The powder obtained had a BET surface area of 114 $m^2/g$ and a loss on ignition of 4.4% by weight. 95 g of the powder were subsequently mixed with 5 g of material which had not been thermally treated (obtained from step (b)) and the mixture was tableted with addition of 2 g of graphite to give shaped bodies having a diameter of 6 mm and a height of 4 mm. The lateral compressive strength based on the pellet weight was 868.2 N/g.

Catalyst 2 (Ex11519.05): The thermal treatment was carried out at 500° C. in a muffle furnace for 3 hours. The powder obtained had a BET surface area of 99 m²/g and a loss on ignition of <0.5% by weight. 95 g of the powder were subsequently mixed with 5 g of material which had not been thermally treated (obtained from step (b)) and the mixture was tableted with addition of 2 g of graphite to give shaped bodies having a diameter of 6 mm and a height of 4 mm. The lateral compressive strength based on the pellet weight was 792.3 N/g.

Catalyst 3 (Ex11519.06): The thermal treatment was carried out at 500° C. in a muffle furnace for 3 hours. The powder obtained had a BET surface area of 99 m²/g and a loss on ignition of <0.5% by weight. 90 g of the powder were subsequently mixed with 10 g of material which had not been thermally treated (obtained from step (b)) and the mixture was tableted with addition of 2 g of graphite to give shaped bodies having a diameter of 6 mm and a height of 4 mm. The lateral compressive strength based on the pellet weight was 894.7 N/g.

Catalyst 4 (Ex11519.07): The thermal treatment was carried out at 500° C. in a muffle furnace for 3 hours. The powder obtained had a BET surface area of 99 m²/g and a loss on ignition of <0.5% by weight. 85 g of the powder were subsequently mixed with 15 g of material which had not been thermally treated (obtained from step (b)) and the mixture was tableted with addition of 2 g of graphite to give shaped bodies having a diameter of 6 mm and a height of 4 mm. The lateral compressive strength based on the pellet weight was 899.1 N/g.

Catalyst 5 (Ex11519.08): The thermal treatment was carried out at 550° C. in a muffle furnace for 3 hours. The powder obtained had a BET surface area of 92 m²/g and a loss on ignition of <0.5° by weight. 95 g of the powder were subsequently mixed with 5 g of material which had not been thermally treated (obtained from step (b)) and the mixture was tableted with addition of 2 g of graphite to give shaped bodies having a diameter of 6 mm and a height of 4 mm. The lateral compressive strength based on the pellet weight was 570.1 N/g.

Catalyst 6 (Ex11519.09): The thermal treatment was carried out at 550° C. in a muffle furnace for 3 hours. The powder obtained had a BET surface area of 92 m²/g and a loss on ignition of <0.5° by weight. 90 g of the powder were subsequently mixed with 10 g of material which had not been thermally treated (obtained from step (b)) and the mixture was tableted with addition of 2 g of graphite to give pellets having a diameter of 6 mm and a height of 4 mm. The lateral compressive strength based on the pellet weight was 620.1 N/g.

Catalyst 7 (Ex11519.10): The thermal treatment was carried out at 550° C. in a muffle furnace for 3 hours. The powder obtained had a BET surface area of 92 m²/g and a loss on ignition of <0.5% by weight. 85 g of the powder were subsequently mixed with 15 g of material which had not been thermally treated (obtained from step (b)) and the mixture was tableted with addition of 2 g of graphite to give shaped bodies having a diameter of 6 mm and a height of 4 mm. The lateral compressive strength based on the pellet weight was 618.4 N/g.

Catalyst 8 (Ex11519.11): The thermal treatment was carried out at 550° C. in a muffle furnace for 3 hours. The powder obtained had a BET surface area of 92 m²/g and a loss on ignition of <0.5% by weight. 80 g of the powder were subsequently mixed with 20 g of material which had not been thermally treated (obtained from step (b)) and the mixture was tableted with addition of 2 g of graphite to give shaped bodies having a diameter of 6 mm and a height of 4 mm. The lateral compressive strength based on the pellet weight was 696.4 N/g.

TABLE 1

Physical properties of the oxidic catalysts obtained after direct tableting to give solid pellets having the dimensions d = 6 mm and h = 4 mm.

|  | BET [m²/g] | LOI [% by wt.] | LCS [N] | LCS [N/g] | PV [mm³/g] |
|---|---|---|---|---|---|
| Comparative catalyst 1 | 92 | 14.0 | 244.5 | 1021.5 | 166.5 |
| Comparative catalyst 2 | 97 | 8.9 | 248.7 | 1020.4 | 192.9 |
| Catalyst 1 | 85 | 7.2 | 216.6 | 868.2 | 186.6 |
| Catalyst 2 | 84 | 4.6 | 194.8 | 792.3 | 202.8 |
| Catalyst 3 | 83 | 5.4 | 218.1 | 894.7 | 208.5 |
| Catalyst 4 | 91 | 6.5 | 224.9 | 899.1 | 180.3 |
| Catalyst 5 | 82 | 0.7 | 126.8 | 570.1 | 289.6 |
| Catalyst 6 | 83 | 1.1 | 142.7 | 620.1 | 222.9 |
| Catalyst 7 | 87 | 1.9 | 140.2 | 618.4 | 221.4 |
| Catalyst 8 | 90 | 2.3 | 156.1 | 696.4 | 241.3 |

Activation of the Catalysts

The catalysts of comparative catalysts 1 and 2 and the catalysts 1 to 4 according to the invention obtained in pellet form were subsequently activated, i.e. reduced in a stream of hydrogen. An amount of in each case 200 ml of the tested catalyst pellets was reduced without application of pressure, i.e. at atmospheric pressure (about 1.01325 bar), in a reaction tube, with the pellets being heated according to a temperature program to 240° C. in flowing reduction gas (900 $l_{gas}/l_{catalyst}$/h) consisting of 2% by volume of hydrogen and about 98% by volume of nitrogen. The temperature was then increased to 250° C. and the reduction was completed in pure hydrogen (400 $l_{gas}/l_{catalyst}$/h). The catalysts were cooled to room temperature under inert gas (nitrogen) and passivated on the surface in a diluted oxygen atmosphere (0.5% by volume of oxygen and about 99.5% by volume of nitrogen) at a maximum of 30° C.

The volume shrinkage of the pellets after reduction and passivation was determined here by measuring the pellet dimensions (diameter and height) of a representative number of 20 pellets. Furthermore, the height of the catalyst bed in the reduction reactor was measured before and after reduction and the shrinkage of the catalyst bed was determined from the difference. Both methods (determination of the pellet shrinkage and determination of the shrinkage of the catalyst bed) are equally suitable for quantifying the shrinkage. Table 2 below shows the values for the average volume shrinkage of the pellets and for the average volume shrinkage of the catalyst bed obtained for the six different shaped catalyst bodies:

TABLE 2

Shrinkage of the catalysts obtained after reduction in a stream of hydrogen.

|  | Volume shrinkage of pellets [%] | Volume shrinkage of catalyst bed [%] |
|---|---|---|
| Comparative catalyst 1 | −10.8 | −11.2 |
| Comparative catalyst 2 | −9.3 | −8.2 |
| Catalyst 1 | −5.9 | −5.3 |
| Catalyst 2 | −0.6 | −2.4 |
| Catalyst 3 | −2.2 | −4.1 |
| Catalyst 4 | −1.9 | −1.1 |

It can be seen from table 1 that the comparative catalysts in the unreduced state have a somewhat higher loss on ignition (and a somewhat higher BET surface area) compared to the catalysts according to the invention. The lower loss on ignition of the shaped catalyst bodies according to the invention correlates with a lower lateral compressive strength based on the pellet weight.

However, the comparative catalysts display a significantly greater volume shrinkage after reduction in a stream of hydrogen (see table 2). While shrinkages in the region of about 10% are observed in the case of the comparative catalysts, the shaped catalyst bodies according to the invention display a significantly decreased shrinkage of from about 6% to less than 1%. The decreased shrinkage combined with a good mechanical strength allows improved utilization of the reactor volume and thus more economical utilization of the shaped catalyst bodies.

In summary, it can thus be said that the shaped catalyst bodies obtainable by the process of the invention are distinguished by a high mechanical strength combined with a greatly decreased shrinkage after reduction.

The invention claimed is:

1. A process for producing a shaped catalyst body containing copper, zinc and aluminum, comprising the steps of:
   (a) combining an alkaline solution with a copper-containing solution obtained by dissolving and/or suspending a copper compound, a zinc compound and an aluminum compound, to form a precipitate;
   (b) isolating the precipitate, with optional washing and/or optional drying thereof, to give a solid catalyst precursor;
   (c) thermally treating a first part of the solid catalyst precursor at a temperature in the range from 450° C. to 600° C. to provide a thermally-treated mixed oxide containing copper, zinc and aluminum, while not thermally treating a second part of the solid catalyst precursor to provide a thermally-untreated solid catalyst precursor containing copper, zinc and aluminum;
   (d) mixing the thermally-untreated solid catalyst precursor with the thermally-treated mixed oxide in a weight ratio of solid catalyst precursor to thermally-treated mixed oxide in the range of 5:95 to 15:85, to give a mixture; and
   (e) tableting the mixture of the thermally-untreated solid catalyst precursor and the thermally-treated mixed oxide obtained in step (d),
   wherein a Cu/Zn atomic ratio of the shaped catalyst body is from 60:40 to 75:25 and a Zn/Al atomic ratio of the shaped catalyst body is from 60:40 to 80:20.

2. The process as claimed in claim 1, wherein the shaped catalyst body has a lateral compressive strength based on the pellet weight of 500 N/g or more.

3. The process as claimed in claim 1, wherein the shaped catalyst body has a loss on ignition of 7.5% by weight or less.

4. The process as claimed in claim 1, wherein the copper-containing solution in step (a) comprises an aluminum hydroxide sol.

5. The process as claimed in claim 1, wherein the copper-containing solution has a pH of 3.0.

6. The process as claimed in claim 1, further comprising the step of:
   (f) reduction of the tableted mixture obtained in step (e).

7. The process as claimed in claim 6, wherein the shaped catalyst body has a volume shrinkage upon reduction of 6% or less.

8. The process as claimed in claim 6, wherein reduction is carried about by means of hydrogen.

9. The process as claimed in claim 1, wherein the Zn/Al atomic ratio of the shaped catalyst body is from 70:30 to 80:20.

10. The process of claim 1, wherein the thermally-untreated solid catalyst is mixed with the mixed oxide in a weight ratio of thermally-untreated solid catalyst precursor to mixed oxide in the range of 10:90 to 15:85.

11. The process of claim 1, wherein the mixed oxide has a BET surface area in the range of 80 m$^2$/g to 140 m$^2$/g.

12. A process for producing a shaped catalyst body containing copper, zinc and aluminum, comprising the steps of:
    mixing an thermally-untreated solid catalyst precursor containing copper, zinc and aluminum with a thermally-treated mixed oxide containing copper, zinc and aluminum in a weight ratio of thermally-untreated solid catalyst precursor to thermally-treated mixed oxide in the range of 5:95 to 15:85, to give a mixture; and
    tableting the mixture of the thermally-untreated solid catalyst precursor and the thermally-treated mixed oxide,
    wherein the thermally-untreated solid catalyst precursor is provided by a method comprising:
      combining an alkaline solution with a copper-containing solution obtained by dissolving and/or suspending a copper compound, a zinc compound and an aluminum compound, to form a precipitate; and
      isolating the precipitate, with optional washing and/or optional drying thereof, but without thermally treating the precipitate, to provide the thermally-untreated solid catalyst precursor; and
    wherein the thermally-treated mixed oxide is provided by a method comprising:
      combining an alkaline solution with a copper-containing solution obtained by dissolving and/or suspending a copper compound, a zinc compound and an aluminum compound, to form a precipitate; and
      isolating the precipitate, with optional washing and/or optional drying thereof, to provide a solid catalyst precursor;
      thermally treating a first part of the solid catalyst precursor at a temperature in the range from 450° C. to 600° C. to provide the thermally-treated mixed oxide; and
    wherein the Cu/Zn atomic ratio of the shaped catalyst body is from 60:40 to 75:25 and the Zn/Al atomic ratio of the shaped catalyst body is from 60:40 to 80:20.

13. The process of claim 12, wherein the Zn/Al atomic ratio of the shaped catalyst body is from 70:30 to 80:20.

14. The process of claim 12, wherein the shaped catalyst body has a lateral compressive strength based on the pellet weight of 500 N/g or more and a loss on ignition of 7.5% by weight or less.

15. The process of claim 12, wherein the first part of the solid catalyst precursor is thermally treated at a temperature in the range from 450° C. to 500° C.

* * * * *